(12) United States Patent
Pavlovsky et al.

(10) Patent No.: US 11,358,939 B2
(45) Date of Patent: Jun. 14, 2022

(54) 1,4-BENZODIAZEPIN-2-ONE DERIVATIVES AND USE THEREOF

(71) Applicant: INNOVATION PHARMACOLOGY RESEARCH OOO ("IPHAR"), Moscow (RU)

(72) Inventors: Viktor Ivanovich Pavlovsky, Moscow (RU); Veniamin Abramovich Khazanov, Moscow (RU); Sergey Aleksandrovich Stankevich, Moscow (RU)

(73) Assignee: INNOVATION PHARMACOLOGY RESEARCH OOO (IPHAR), Tomsk (RU)

( * ) Notice: Subject to any disclaimer, the term of this patent is extended or adjusted under 35 U.S.C. 154(b) by 0 days.

(21) Appl. No.: 16/766,649

(22) PCT Filed: Dec. 29, 2018

(86) PCT No.: PCT/RU2018/000907
§ 371 (c)(1),
(2) Date: May 22, 2020

(87) PCT Pub. No.: WO2019/103658
PCT Pub. Date: Mar. 31, 2019

(65) Prior Publication Data
US 2020/0361878 A1    Nov. 19, 2020

(30) Foreign Application Priority Data

Nov. 24, 2017   (RU) .................................. 201714001

(51) Int. Cl.
*A61K 31/5513*    (2006.01)
*A61P 25/04*    (2006.01)
(Continued)

(52) U.S. Cl.
CPC .................................. C07D 243/24 (2013.01)

(58) Field of Classification Search
CPC ...... A61K 31/5513; A61P 25/04; A61P 25/24; A61P 25/28; C07D 243/24
See application file for complete search history.

(56) References Cited

FOREIGN PATENT DOCUMENTS

| UA | 102273 C2 | 6/2013 |
|---|---|---|
| WO | 2004106310 A1 | 12/2004 |
| WO | 201 9103658 A3 | 5/2019 |

OTHER PUBLICATIONS

Edward K. Dzladulewlcz, et al., The Design of Non-Peptide Human Bradykinin B 2 Receptor Antagonists Employing the Benzodiazepine Peptidomimetic Scaffold, Bioorganic & Medicinal Chemistry Letters 9 (1999) 463-468.

(Continued)

*Primary Examiner* — Brenda L Coleman

(74) *Attorney, Agent, or Firm* — Dergosits & Noah LLP

(57) ABSTRACT

The invention relates to novel compounds that are derivatives of 1,4-benzodiazepin-2-one, having the general formula I:

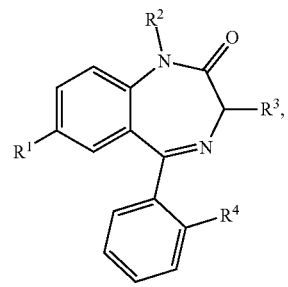

and being limited to structural variants 1-6:

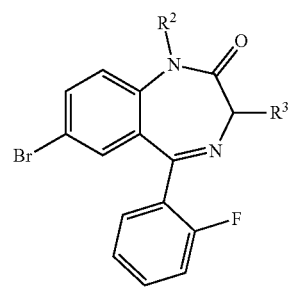

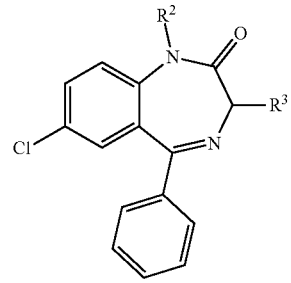

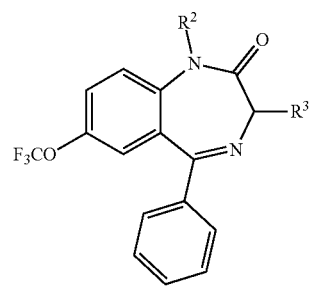

(Continued)

-continued

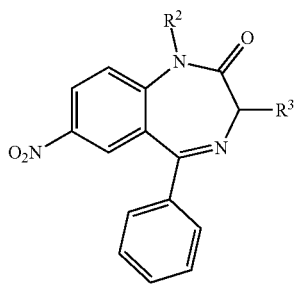

4

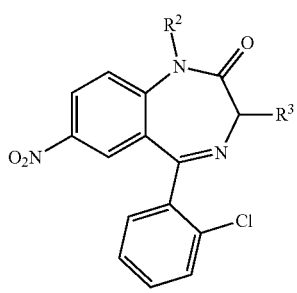

5

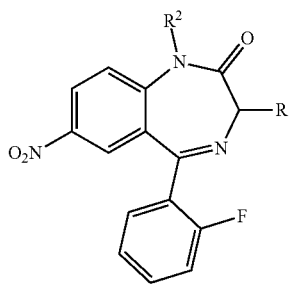

6 on condition that:
a) structures 1 ($R^1$=Br, $R^4$=F), 3 ($R^1$=OCF$_3$, $R^4$=H), 5 ($R^1$=NO$_2$, $R^4$=Cl) and 6 ($R^1$=NO$_2$, $R^4$=F) have the following substituents $R^2$ and $R^3$:

$R^2$=H, CH$_2$COCH$_3$, CH$_2$COOCH$_3$, CH$_2$CONHNH$_2$;
$R^3$=OAlk, NHAr, where
  Alk=C$_2$H$_5$, C$_3$H$_7$, C$_4$H$_9$, (CH$_2$)$_2$OH, (CH$_2$)$_2$OCH$_3$,

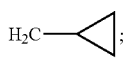

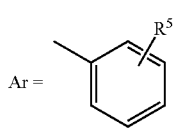

$R^5$=o-, m-, p-COCH$_3$, Cl, F, Br, NO$_2$, CF$_3$;
b) structure 2 ($R^1$=Cl, $R^4$=H) has the following substituents $R^2$ and $R^3$:
  if $R^2$=H,
  then $R^3$=OAlk, NHAr, where
    Alk=(CH$_2$)$_2$OCH$_3$,

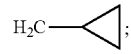

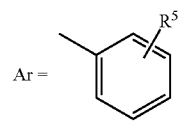

$R^5$=m-, p-COCH$_3$, o-, m-, p-F, Br, CF$_3$;
  if $R^2$=CH$_2$COCH$_3$, CH$_2$COOCH$_3$, CH$_2$CONHNH$_2$,
  then $R^3$=OAlk, NHAr, where
    Alk=C$_2$H$_5$, C$_3$H$_7$, C$_4$H$_9$, (CH$_2$)$_2$OH, (CH$_2$)$_2$OCH$_3$,

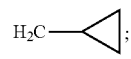

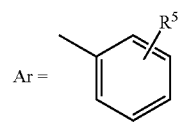

$R^5$=o-, m-, p-COCH$_3$, Cl, F, Br, NO$_2$, CF$_3$;
c) structure 4 ($R^1$=NO$_2$, $R^4$=H) has the following substituents $R^2$ and $R^3$:
  if $R^2$=H,
  then $R^3$=OAlk, NHAr, where
    Alk=(CH$_2$)$_2$OCH$_3$,

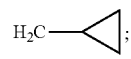

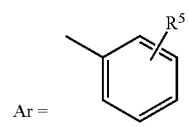

$R^5$=o-, m-, p-COCH$_3$, Cl, F, Br, NO$_2$, CF$_3$;
  if $R^2$=CH$_2$COCH$_3$, CH$_2$COOCH$_3$, CH$_2$CONHNH$_2$,
  then $R^3$=OAlk, NHAr, where
    Alk=C$_2$H$_5$, C$_3$H$_7$, C$_4$H$_9$, (CH$_2$)$_2$OH, (CH$_2$)$_2$OCH$_3$,

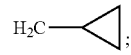

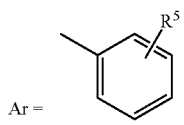

Ar =

$R^5$=o-, m-, p-COCH$_3$, Cl, F, Br, NO$_2$, CF$_3$ and the use of said compounds in the field of medicine as analgesics, anorexigenic or orexigenic agents for weight regulation (loss or gain), antidepressants and anxiolytics for treating psychological disorders, and also antihypoxic and nootropic agents for the prophylaxis and treatment of central nervous system disorders.

3 Claims, No Drawings

(51) Int. Cl.
    *A61P 25/24*     (2006.01)
    *A61P 25/28*     (2006.01)
    *C07D 243/24*     (2006.01)

(56) References Cited

OTHER PUBLICATIONS

Michael R. Wood et al., Benzodiazepines as Potent and Selective Bradykinin B1 Antagonists, J. Med. Chem. 2003, 46, 1803-1806.
Frederick Petty et al., Benzodiazepines as Antidepressants:Does GABA Play a Role in Depression?, Biol Psychiatry 1995:38:578-591.
Furukawa et al., Antidepressants plus benzodiazepines for major depression (Review), Cochrane Database of Systematic Reviews. 2001, Issue 3. Art. No. CD001026.
Kunchandy et al., Hydroxic Stress-Induced Convulsion and Death: Protective Effect of a2-Adrenoceptor and Benzodiazepine Receptor Agonists and Ro5-4864, Arch. int. Pharmacodyn. 292. 35-44 (1988).
Stevens et al., National, regional, and global trends in adult overweight and obesity prevalences, Population Health Metrics, 2012, 10:22, http://populationhealthmetrics.com.content/10/1/22.
Katherine A. Halmi et al., The Relation among Perfectionism, ObsessiveCompulsive Personality Disorder and DbsessiveCompulsive Disorder in Individuals with Eating Disorders, Int J Eat Disord 2005; 38:371-374.
M. Edward Pierson et al., CCK Peptides with Combined Features of Hexa- and Tetrapeptide CCK-A Agonists, J. Med. Chem., 2000, 43, 2350-2355.
Vijay K. Yadav, A Serotonin-Dependent Mechanism Explains the Leptin Regulation of Bone Mass, Appetite, and Energy Expenditure, Cell 138, 976-989, Sep. 4, 2009 ᵃ2009 Elsevier Inc.
R. D. Porsolt, Animal Model of Depression, Biomedicine, 1979, 30, 139-140.
T. L. Karaseva et al., Synthesis of New 7-Bromo-5-(2'-Chlorophenyl)-3-Arylamino-1,2-Dihydro-3H-1,4-Benzodiazepine Derivatives and Their Influence on Appetite in Rats, Pharmaceutical Chemistry Journal, vol. 51, No. 4, Jul. 2017 (Russian Original vol. 51, No. 4, Mar. 2017).
V. I. Pavlovskii et al., Synthesis and Analgesic Activity of 3-Arylamino-1,2-Dihydro-3H-1,4-Benzodiazepin-2-Ones, Pharmaceutical Chemistry Journal, vol. 49, No. 9, Dec. 2015 (Russian Original vol. 49, No. 9, Sep. 2015).
V. I. Pavlovsky et al., Analgesic Effects of 3-Substituted Derivatives of 1,4-Benzodiazepines and their Possible Mechanisms, Neurophysiology, vol. 45, Nos. 5/6, Nov. 2013.
V. I. Pavlovsky et al., Synthesis and Anticonvulsant Activity of 3-Alkoxy-1,2-Dihydro-3H-1,4-Benzodiazepin-2-Ones, Pharmaceutical Chemistry Journal, vol. 46, No. 9, Dec. 2012 (Russian Original vol. 46, No. 9, Sep. 2012).
Sergey Andronati et al., Synthesis, structure and affinity of novel 3-alkoxy-1,2-dihydro-3H-1,4-benzodiazepin-2-ones for CNS central and peripheral benzodiazepine receptors, European Journal of Medicinal Chemistry 45 (2010) 1346-1351.
Michael Offel et al., Synthesis of Substituted 3-Anilino-5-phenyl-1,3-dihydro-2H-1,4-benzodiazepine-2-ones and their Evaluation as Cholecystokinin-Ligands, Arch. Pharm. Chem. Life Sci. 2006, 339, 163-173.
S. Yu. Makan et al., Molecular Targets of New 1,4-Benzodiazepin-2-One Derivatives Influencing the Appetite of Experimental Animals, Pharmaceutical Chemistry Journal, vol. 39, No. 6, 2005.
Shen K. Yang, Racemization and Stereoselective Alcoholysis of Temazepam, Chirality 11:179-186 (1999).
International Search Report and Written Opinion for PCT/RU2018/000907, dated Jun. 13, 2019.
Gacura V.V. Methods of preliminary pharmacological research of biologically active compounds. M.: Medicine. 1974. 144 p.
Prozorovsky V.B. Statistical processing of the results of pharmacological research. Psychopharmacology and biological narcology. 2007. V. 7 No. 3-4 p. 2090-2120.
Andronati S.A., Avrucky G.Y.,Voronina T.A., et al. Phenazepam, edited by Bogatsky A.V., K.: Naukova Dumka, 1982, p. 288.
K. S. Andronati,E. A. Kostenko,T. L. Karaseva, and S. A. Andronati. Synthesis and Pharmacological Properties of 3-Amino-1,2-Dihydro-3H-1,4-Benzodiazepin-2-One Derivatives. Pharmaceutical Chemistry Journal, vol. 36, No. 7, 2002. Translated from Khimiko-Farmatsevticheskii Zhurnal, vol. 36, No. 7, pp. 16-18, Jul. 2002. Original article submitted Mar. 14, 2002.
S. A. Andronati, T. L. Karaseva, A. A. Kazakova, V. I. Pavlovskii, and S. Yu. Bachinskii. Synthesis and Neurotropic Properties of Arylidene-1,2-Dihydro-3H-1,4-Benzodiazepin-2-Ones. Pharmaceutical Chemistry Journal, vol. 45, No. 4, Jul. 2011 (Russian Original vol. 45, No. 4, Apr. 2011). Translated from Khimiko-Farmatsevticheskii Zhurnal, vol. 45, No. 4, pp. 19-20, Apr. 2011. Original article submitted Feb. 6, 2009.

1,4-BENZODIAZEPIN-2-ONE DERIVATIVES AND USE THEREOF

CROSS-REFERENCE TO RELATED APPLICATIONS

This present application claims the benefit of International Application No. PCT/RU2018/000907, entitled, "1,4-BENZODIAZEPIN-2-ONE DERIVATIVES AND USE THEREOF", filed Dec. 29, 2018, which claims priority to Russian Application No. 201714001, entitled, "1,4-BENZODIAZEPIN-2-ONE DERIVATIVES AND USE THEREOF", filed Nov. 24, 2017. The contents of International Application No. PCT/RU2018/000907 and Russian Application No. 201714001 are incorporated herein by reference.

FIELD OF THE INVENTION

The invention relates to organic chemistry, pharmacology and medicine, in particular, to compounds of benzodiazepine series, which can be used for pain treatment (analgesic), weight regulation, treatment of medical disorders, obsessive disorders, panic attacks and other central nervous system disorders.

DESCRIPTION OF THE PRIOR ART 1,4-benzodiazepine derivatives are widely used in medicine, since they have hypnotic, sedative, anxiolytic, myorelaxant and anticonvulsive action. Over 50 pharmaceutical substances based on 1,4-benzodiazepines are included in different drugs used to prevent and treat different central nervous system disorders as anxiolytic medications (tranquilizers) and as hypnotic and anticonvulsant drugs.

Over the last 20 years great progress was made in the chemistry and pharmacology of 1,4-benzodiazepines: many new compounds—ligands of benzodiazepine sites of GABAA receptors were synthesized, some of which, in addition to anxiolytic properties, also have analgesic, anorexigenic, antidepressant, antihypoxic, nootropic and other properties.

In particular, it was discovered that 1,4-benzodiazepine derivatives, that have amide residues in the third position, exert considerable analgesic activity and high affinity to the receptors of bradykinin—a potent natural pain inducer [1,2].

It's also known that some 3-substituted-1,2-dihydro-3H-1,4-benzodiazepin-2-ones have not only analgesic activity, but also anorexigenic, antidepressant, antihypoxic, nootropic and other types of activity. Pharmacological properties of these compounds are mediated by their binding with the receptors of benzodiazepine, cholecystokinin and bradykinin [3, 4, 5, 6, 7].

Thus, synthesis of new 1,4-benzodiazepine derivatives is a promising approach for creating new drugs for solving relevant medical problems: pain alleviation, weight regulation and treatment of different disorders of central nervous system.

Chronic pain of different causes and the accompanying depression, anxiety and insomnia pose a serious medical and social problem. Modern analgesic drugs are either not effective enough (in case of non-steroidal anti-inflammatory drugs) or have dangerous adverse effects, especially prominent in narcotic analgesic drugs.

Over 1 billion people worldwide suffer from excessive weight and obesity [8], which poses a serious medical problem, since it increases the risk of diabetes, cardiovascular and other diseases. On the other hand, advertising of thinness, lack of appetite, severe body mass loss in diseases such as tuberculosis, cancer, AIDS, leads to an increase in the number of people with anorexia [9]. This increases the interest in the problem of weight regulation and eating behavior.

An important task of modern pharmacology is the search for drugs increasing human life expectancy and survival in conditions of severe hypoxia. The existing antihypoxic and nootropic drugs do not fully satisfy the requirements of practical medicine.

Treatment of depression remains a highly relevant problem. The incidence of depressive disorders in the population is growing, including masked depressions with somatovegetative component. According to the WHO data, worldwide over 110 million people (3-6% of the population) have clinically significant manifestations of depression.

The closest compound to the disclosed compounds, 1,4-benzodiazepin-2-one derivatives, in chemical structure and pharmacology, a prototype of the invention, is methyl-2-(7-bromo-3-etoxy-2-oxo-5-phenyl-2,3-dihydro-1H-benzo[e][1,4]diazepin-1-yl) acetate, which demonstrates analgesic activity in acetic acid-induced writing test with $ED_{50}=0.47\pm0.15$ mg/kg [10]:

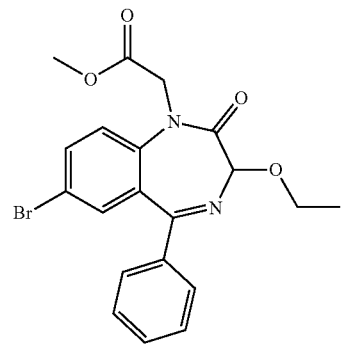 [SMILES: CCOC1N=C(c2ccccc2)c2cc(Br)ccc2N(CC(=O)OC)C1=O]

Analogs of the disclosed compounds, 1,4-benzodiazepin-2-one derivatives, in certain types of pharmacological activity are: sodium diclofenac, demonstrating analgesic activity in acetic acid-induced writing test with $ED_{50}=10.0\pm1.8$ mg/kg; the hormone leptin, which reduces appetite and body mass but doesn't have antihypoxic and antidepressant activity; antidepressant amitriptyline which has potent antidepressant effect, but doesn't have antihypoxic action and doesn't affect the appetite.

SUMMARY OF THE INVENTION

The goal of the present invention is to widen the range of pharmacologically active benzodiazepine compounds by using 3-substituted-1,2-dihydro-3H-1,4-benzodiazepin-2-ones of general formula I:

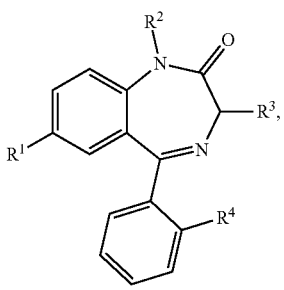

as potential medical drugs, having analgesic activity, regulating appetite and body weight, having antihypoxic, nootropic, antidepressant and anxiolytic properties.

DETAILED DESCRIPTION OF THE INVENTION

The goal is solved by the synthesis of 3-substituted-1,2-dihydro-3H-1,4-benzodiazepin-2-ones of general formula I, including its variants:

a) 1-substituted 3-alcoxy-1,3-dihydro-2H-benzo[e][1,4]diazepin-2-ones of general formula Ia;

b) 1-substituted 3-arylamino-1,3-dihydro-2H-benzo[e][1,4]diazepin-2-ones of general formula Ib.

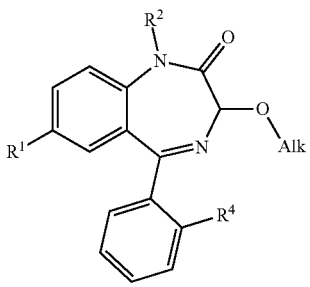

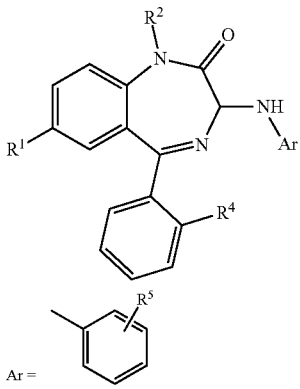

Embodiment 1

Table 1 lists the synthesized 1-substituted 3-alcoxy-1,3-dihydro-2H-benzo[e][1,4]diazepin-2-ones (Ia).

General Method of Synthesis of 1-substituted 3-alcoxy-1,3-dihydro-2H-benzo[e][1,4]diazepin-2-ones (Ia) (№№ 1-82, Table 1)

7-nitro-5-phenyl-3-propoxy-1,3-dihydro-2H-benzo[e][1,4]diazepin-2-one 1 g (3.367 mmol) of 3-hydroxy-7-nitro-5-phenyl-1,3-dihydro-2H-benzo[e][1,4]diazepin-2-one is put into a 100 ml flask, 50 ml of anhydrous chloroform is added, then 1.0 ml (13.78 mmol) of thionyl chloride is added, the mixture is boiled for 40 min, the precipitate is dissolved, then 5 ml of anhydrous 1-propanol is added. The mixture is boiled for 1 hours, rinsed with water (5×5 ml), chloroform is evaporated at a rotary evaporator. The precipitate is crystallized from xylol. Yield=79%, (0.9 g); melting point=220-222° C.

Methyl-2-(7-nitro-2-oxo-5-phenyl-3-propoxy-2,3-dihydro-1H-benzo[e]

[1,4]di-azepin-1-yl)acetate (№ 48 in Table 1)

1 g (3.367 mmol) of 7-nitro-5-phenyl-3-propoxy-1,3-dihydro-2H-benzo[e][1,4]diazepin-2-one is put into a 100 ml flask, 40 ml of dioxane is added, then 20 ml of saturated potassium carbonate solution is added, 10 mg of tetrabutylammonium iodide is added, then 1.5 ml (15.78 mmol) of methylbromoacetate is added. The reaction mixture is stirred at room temperature for 2-3 hours. Dioxane is separated at a separation funnel and evaporated at a rotary evaporator. The precipitate is crystallized from xylol. Yield=65.0%, (0.9 g); melting point=214-215° C., needle-like white to off white crystals. Compounds №№ 1-47, 49-82 in Table 1 are produced in a similar way).

Embodiment 2

Table 2 lists 1-substituted 3-arylamino-1,3-dihydro-2H-benzo[e][1,4]diazepin-2-ones of general formula Ib.

General Method of synthesizing 1-substituted 3-arylamino-1,3-dihydro-2H-benzo[e][1,4]diazepin-2-ones (Ib) (№№ 83-400 in Table 2)

7-nitro-5-phenyl-3-(2-nitrophenyl)amino-1,3-dihydro-2H-benzo[e][1,4]diazepin-2-one (№ 275 in Table 2)

1 g (3.367 mmol) of 3-hydroxy-7-nitro-5-phenyl-1,3-dihydro-2H-benzo[e][1,4]diazepin-2-one is put into a 100 ml flask, 50 ml of anhydrous chloroform is added, then 1.0 ml (13.78 mmol) of thionyl chloride is added, the mixture is boiled for 40 min, the precipitate is dissolved, then 0.93 g (6.73 mmol) of 2-nitroaniline is added. The mixture is boiled for 1 hours, rinsed with water (5×5 ml), chloroform is evaporated at a rotary evaporator. The precipitate is crystallized from ethanol. Yield=64%, (0.9 g); melting point=225-227° C.

Methyl-2-(7-nitro-2-oxo-5-phenyl-3-(2-nitrophenyl)amino-2,3-dihydro-1H-benzo[e][1,4]di-azepin-1-yl)acetate (№ 278 in Table 2)

1 g (3.367 mmol) of 7-nitro-5-phenyl-(2-nitrophenyl)amino-1,3-dihydro-2H-benzo[e][1,4]diazepin-2-one (№ 275 in Table 2) is put into a 100 ml flask, 40 ml of dioxane is added, then 20 ml of saturated potassium carbonate solution is added, 10 mg of tetrabutylammonium iodide is added, then 1.5 ml (15.78 mmol) of methylbromoacetate is added. The reaction mixture is stirred at room temperature for 2-3 hours. Dioxane is separated at a separation funnel and evaporated at a rotary evaporator. The precipitate is crystallized from xylol. Yield=65.0%, (0.9 g); melting point=218-220° C., yellow crystals. Compounds №№ 83-274, 276, 277, 279-400 in Table 2 are produced in a similar way).

Embodiment 3. Affinity of Compounds Ia to Central and Peripheral Benzodiazepine Receptors Affinity of the compounds to central benzodiazepine receptors (CBR) was studied using radioreceptor method of competitive displacement of radioligant [$^3$H]-flumazenil ($R_o$ 15-1788) from its specific binding sites at the receptor. Ligand displacement were performed in $1\times10^{-6}$ mol/L concentration.

Data on the affinity of 3-alcoxy-1,3-dihydro-2H-benzo[e][1,4]diazepin-2-ones (Ia) to central and peripheral benzodiazepine receptors is presented in Table 3.

Embodiment 4. Assessment of Analgesic Activity of Compounds of General Formula I Assessment of analgesic activity was performed in a model of peripheral pain based on chemical pain induced by intraperitoneal administration of acetic acid, leading to involuntary contractions of abdominal muscles, termed "writhes", accompanied by hind leg extension and spine arching. The writhes were induced by 0.75% solution of acetic acid, which was administered intraperitoneally 40 min after intraperitoneal administration of test compounds in 0.001-5 mg/kg dose range. The animals were observed for 20 min and the number of writhes in each animal was counted. Analgesic activity was assessed by the ability of the compounds to reduce the number of writhes in test group compared to control group, and indicated as percentage using the following formula:

$$AA=(W_c-W_t/W_c)\times100\%,$$

where AA—analgesic activity in %;
$W_c$—average number of writhes in control group;
$W_t$—average number of writhes in test group Test compounds were studied in comparison with the reference drug sodium diclofenac in 10 mg/kg dose [11]. $ED_{50}$ was calculated using Prozorovsky method [12].

As the data in Table 4 shows, all studied derivatives of 3-alcoxy-1,3-dihydro-2H-benzo[e][1,4]diazepin-2-ones (Ia) exert potent analgesic action, inhibiting writhes in animals in 1 mg/kg dose by 45-88% compared to control. For certain derivatives of Ia (№№ 21, 22, 44, 45, 48 in Table 4) effective dose $ED_{50}$ was determined, which was: 0.29±0.025; 0.08±0.02; 0.07±0.02; 0.047±0.014; 0.058±0.015, respectively. $ED_{50}$ values of reference drugs were: 1.50±0.26 mg/kg for indomethacin, 10.0±1.8 mg/kg for sodium diclofenac. Thus, the disclosed compounds of formula Ia have more potent analgesic activity than the reference drugs, since they have a much lower (by 1-2 orders of magnitude) $ED_{50}$ value.

The derivatives of 3-arylamino-1,3-dihydro-2H-benzo[e][1,4]diazepin-2-ones (Ib) also have potent analgesic activity, inhibiting writhes in animals in 1 mg/kg dose by over 50% (data on their analgesic activity is presented in Table 5).

Studies of pharmacological activity of 3-arylamino-1,3-dihydro-2H-benzo[e][1,4]diazepin-2-ones, namely, their action of appetite, assessment of antihypoxic and antidepressant activity was performed in white male rats with body mass 150-180 g and male mice with body mass 18-22 g. The animals were kept on a standard laboratory diet and natural lighting. Animals of control group were given a water-Tween suspension. Test compounds were administered in a suspension with Tween-80 Reference drugs were the hormone leptin, in 0.0002 mg/kg dose, and a well-known antidepressant amitriptyline (solution for injections in 1 ml vials. Test compounds and the water-Tween suspension were administered in a dose of 0.2 ml/100 g of rat body mass.

Embodiment 5. Assessment of Action on Appetite (Anorexigenic Action) of Compounds of Formula Ib The action of the compounds on rat appetite was studied using «norexia» method. For 2 weeks in an experimental equipment the rats were conditioned to consume liquid food. Then a water-Tween suspension of test articles was administered intraperitoneally to conditioned animals one day before the experiment. After 40 minutes the animals were allowed access to liquid food and the amount of consumed food (in ml) of every rat was registered every 30 minutes for 3 hours. The next day after 2 hours of deprivation the rats in control group were administered a water-Tween suspension intraperitoneally, while the test group was administered the test articles. After 40 minutes the animals were allowed access to liquid food and the amount of consumed food (in ml) of every rat was registered every 30 minutes for 3 hours. Then all food consumption values for each rat were summed and compared to control values. The control group has consumed on average 7 ml of liquid food per 30 minutes. The effect was calculated in percentage compared to control [13].

Effect of 3-arylamino-1,3-dihydro-2H-benzo[e][1,4]diazepin-2-ones (Ib) on food consumption by rats, assessed using «Anorexia» method, is presented in Table 6.

Among test articles compounds №№ 194, 248 and 356 (Table 6) have anorexigenic action, as evidenced by the reduction in appetite and food consumption by the studied rats by 47%, 41% and 39%, respectively, compared to control (Table 6).

The hormone leptin has reduced appetite and food consumption by 63% compared to control. It should be noted that compound № 358 (Table 6) had a hyperphagic effect, i.e. increased the appetite.

Embodiment 6. Assessment of Antihypoxic Activity of Compounds Ib

Screening of antihypoxic activity was performed using the model of acute confined space hypoxia (CSH). CSH was modeled by placing mice into isolated sealed chambers (V=200 ml). Each group included 10 animals. The observation lasted until the death of the animals. Antihypoxic effect was assessed by the survival duration (in min) compared to control, which was taken as 100%, and according to the calculation of antihypoxic protection ratio ($R_{pr}$): $R_{pr}=T_t/T_c$, where $T_t$—average animal survival time in the test group; $T_c$—average animal survival time in the control group [11].

The advantage of the test compound over the reference drug, the hormone leptin, is the presence of potent antihypoxic and antidepressant activity, in addition to high anorexigenic activity. It was shown, that the derivatives of 3-arylamino-1,3-dihydro-2H-benzo[e][1,4]diazepin-2-ones in 10 mg/kg dose have antihypoxic action in a model of acute confined space hypoxia in mice. The highest efficacy was observed in compounds № 250 and 357, the action of which increased mice survival time during acute confined space hypoxia by 70% and 40.5%, respectively, compared to control. The reference drug, hormone leptin, had no antihypoxic properties [14].

Embodiment 7. Assessment of Antidepressant Activity of Compounds Ib

Antidepressant activity was studied using «Porsolt forced swimming test» [15], which models stress in mice by forcing them to swim in a narrow translucent cylinder, filled by ⅓ volume with water at 23-25° C. temperature. Antidepressant action is assessed by the reduction in immobility time, when the animals have minimal amount of paddling, in seconds or percentage compared to control. The animal behavior was registered for 4 minutes after acclimatization for 2 minutes.

Study of action of 3-arylamino-1,3-dihydro-2H-benzo[e][1,4]diazepin-2-ones of formula Ib on mice immobility time in forced swimming test has shown that all test compounds in 1 mg/kg dose have antidepressant effects. Compounds № 159 and № 194 have the most potent antidepressant action, reducing immobility time in mice by 32% and 40%, respectively, compared to control, being as effective as the reference drug amitriptyline in 1 mg/kg dose (40%). The hormone leptin in 0.0002 mg/kg dose reduces immobility time by only 14% compared to control, i.e. it has a weak antidepressant effect.

The performed studies have shown that among 3-arylamino-1,3-dihydro-2H-benzo[e][1,4]diazepin-2-ones of formula 1b there are compounds having potent anorexigenic activity and interesting for further research as potential medical drugs, regulating eating behavior and reducing appetite and body mass. The advantage of the disclosed compounds over the reference drugs is the additional presence of potent antihypoxic and antidepressant activity compared to the reference drugs amitriptyline and the hormone leptin.

Embodiment 8. Assessment of Anxiolytic Activity of Compounds Ib

Anxiolytic activity was assessed in a model of conflict situation based on the conflict of two reflexes (drinking and defensive) when drinking water from a water fountain. Anxiolytic activity was assessed by the number of drinking actions despite electric shock [16].

General movement activity was assessed in an open field test. While the animals were in the open field (3 min), the number of rearings (vertical movement activity), transitions between squares (horizontal movement activity) and the number of explored holes (exploratory activity) were registered. The sum of these values is general movement activity [17].

Diazepam drug was used as the reference drug. All test compounds and the reference drug diazepam were administered in a suspension with Tween-80 in 5 mg/kg dose 30 min before the start of experiments.

Anxiolytic properties and action on general movement activity of 1-methoxy-carbonylmethyl-3-arylamino-1,3-dihydro-2H-benzo[e][1,4]diazepin-2-ones (Ib) is presented in Table 7.

Table 7 shows that compounds №№ 173, 227 and № 281 had potent anxiolytic properties, while compounds №№ 89, 317, 327, 363 and № 399 don't have sedative properties, their general movement activity values didn't statistically differ from animals of the control group.

Thus, many of the synthesized compounds—derivatives of 1,4-benzodiazepin-2-one of general formula I, including compounds of formula Ia and compounds of formula Ib, have potent analgesic action. The disclosed compounds may be used as non-opioid analgesics for treating pain of different causes and intensity. At the same time, among 3-arylamino-1,3-dihydro-2H-benzo[e][1,4]diazepin-2-ones of formula Ib, unlike the compounds of formula Ia, compounds with high anorexigenic activity were discovered, manifested in the reduction in appetite and body mass in rats under effect of the test compounds in low doses 0.1-0.05 mg/kg using "Anorexia" method compared to control and the reference drug—satiation hormone leptin (0.0002 mg/kg).

In addition to anorexigenic activity, the disclosed compounds of formula Ib have antihypoxic, antidepressant and anxiolytic properties, which makes them different from the reference drugs—satiation hormone leptin and amitriptyline. Therefore compounds of formula Ib, in addition to their use as analgesics, can also be used to regulate weight (gain or loss) as anorexigenic or orexigenic drugs, treat mental disorders as antidepressant and anxiolytic drugs, and also to prevent and treat disorders of CNS functioning as antihypoxic and nootropic drugs.

REFERENCES CITED

1. Dziadulewicz E. K., Brown M. C., Dunstan A. R. et al. The design of non-peptide human bradykinin B2 antagonists employing the benzodiazepine peptidomimetic scaffold. Bioorg. Med. Chem. Lett. 1999. V. 9 P. 463-468.
2. Wood M. R., Kim J. J., Han V et al. Benzodiazepines as Potent and Selective Bradykinin B1 Antagonists. J. Med. Chem. 2003. V. 46 N 10 P. 1803-1806.
3. Andronati K. S., Kostenko E. A, Karaseva T. L., Andronati S. A. Synthesis and pharmacological properties of derivatives of 3-amino-1,2-dihydro-3H-,4-benzodiazepin-2-one. Chem.-Pharm. J. 2002. V. 36 № P. 16-18.
4. Andronati S. A., Karaseva T. L., Kazakova A. A., Pavlovsky V. I., Bachinskiy S. Y. Synthesis and neurotropic properties of 3-aryliden-1,2-dihydro-3H-1,4-benzodiazepin-2-ones. Chem.-Pharm. J. 2011. V. 45 № 4 P. 101-102.
5. Petty F., Trivedi M. H., Fulton M., and Rush A. J. Benzodiazepines as antidepressants: Does GABA play a role in depression? Biol Psychiatry. 1995. November 1; 38(9):578-591.
6. Furukawa T. A., Streiner D., Young L. T., Kinoshita Y. Antidepressants plus benzodiazepines for major depression (Review) Cochrane Database of Systematic Reviews 2001, Issue 3. Art. No.: CD001026. DOI: 10.1002/14651858.CD001026
7. Kunchandy J., Kulkarni S. K. Hypoxic stress-induced convulsion and death: protective effect of alpha 2-adrenoceptor and benzodiazepine receptor agonists and Ro 5-4864. Arch Int Pharmacodyn Ther. 1988, 292:35-44.
8. Stevens G. A., Singh G. M., Lu Y. et al. National, regional, and global trends in adult overweight and obesity prevalences. Population Health Metrics. 2012. 10:22 https://doi.org/10.1186/1478-7954-10-22.
9. Halmi K. A., Tozzi F., Thornton L. M., et al. The relation among perfectionism, obsessive-compulsive personality disorder, and obsessive-compulsive disorder in individuals with eating disorders. International Journal of Eating Disorders. 2005. V. 38 P. 371-374. DOI:10.1002/eat.20190

10. Ukrainian patent № 102273 "3-alkoxy-1,2-dihydro-3h-1,4-benzodiazepine-2-ones exhibiting high analgetic activity"/V. I. Pavlovsky, K. O. Semenishyna, S. A. Andronati et al. — № a 2011 05837. Appl. 10 May 2011. Publ. 25 Jun. 2013. Bul. № 12.
11. Gacura V. V. Methods of preliminary pharmacological research of biologically active compounds. M.: Medicine. 1974. 144 p.
12. Prozorovsky V. B. Statistical processing of the results of pharmacological research. Psychopharmacology and biological narcology. 2007. V. 7 № 3-4 P. 2090-2120.
13. Pierson M. E. et al. CCK Peptides with combined features of hexa- and tetrapeptide CCK-A agonists. J. Med Chem. 2000. Vol. 43 N 12 P. 2350-2355.
14. Yadav V. K., Oury F., Suda N. et al. A Serotonin-Dependent Mechanism Explains the Leptin Regulation of Bone Mass, Appetite, and Energy Expenditure. Cell. 2009. Vol. 138 Issue 5 P. 976-938. https://doi.org/10.1016/j.cell.2009.06.051
15. Porsolt R. D. Animal model of depression. Biomed. 1979. V. 30 (3). P. 139-140.
16. Andronati S. A., Avrucky G. Y., Voronina T. A., et al. Phenazepam, edited by Bogatsky A. V., K.: Naukova Dumka, 1982, P. 288.
17. Vychlaev Y. I., Voronina T. A. Phenazepam pharmacology. Express-inform. VNIIMI—New drugs. 1978. № 3. P. 2-16.

1,4-benzodiazepin-2-one Derivatives and Use Thereof

TABLE 1

The list of synthesized 1-substituted 3-alcoxy-1,3-dihydro-2H-benzo[e][1,4]diazepin-2-ones

| No | $R^1$ | $R^2$ | Alk | $R^4$ | Melting point, °C | Yield, % |
|---|---|---|---|---|---|---|
| 1 | Br | H | $C_2H_5$ | F | 205-208 | 60 |
| 2 | Br | H | $C_3H_7$ | F | 185-187 | 66 |
| 3 | Br | H | $C_4H_9$ | F | 192-195 | 65 |
| 4 | Br | H | $(CH_2)_2OH$ | F | 120-123 | 75 |
| 5 | Br | H | $(CH_2)_2OCH_3$ | F | 178-180 | 44 |
| 6 | Br | H | $H_2C$—△ | F | 221-223 | 40 |
| 7 | Br | $CH_2COCH_3$ | $C_2H_5$ | F | 172-175 | 61 |
| 8 | Br | $CH_2COCH_3$ | $C_3H_7$ | F | 175-177 | 65 |
| 9 | Br | $CH_2COCH_3$ | $C_4H_9$ | F | 155-157 | 59 |
| 10 | Br | $CH_2COOCH_3$ | $C_2H_5$ | F | 181-182 | 57 |
| 11 | Br | $CH_2COOCH_3$ | $C_3H_7$ | F | 183-185 | 52 |
| 12 | Br | $CH_2COOCH_3$ | $C_4H_9$ | F | 177-179 | 48 |
| 13 | Br | $CH_2CONHNH_2$ | $C_2H_5$ | F | 202-205 | 57 |
| 14 | Br | $CH_2CONHNH_2$ | $C_3H_7$ | F | 207-209 | 63 |
| 15 | Br | $CH_2CONHNH_2$ | $C_4H_9$ | F | 205-206 | 65 |
| 16 | Cl | H | $(CH_2)_2OCH_3$ | H | 210-212 | 41 |
| 17 | Cl | H | $H_2C$—△ | H | 242-245 | 43 |
| 18 | Cl | $CH_2COCH_3$ | $C_2H_5$ | H | 172-173 | 62 |
| 19 | Cl | $CH_2COCH_3$ | $C_3H_7$ | H | 177-179 | 61 |
| 20 | Cl | $CH_2COCH_3$ | $C_4H_9$ | H | 165-167 | 53 |
| 21 | Cl | $CH_2COOCH_3$ | $C_2H_5$ | H | 183-185 | 51 |
| 22 | Cl | $CH_2COOCH_3$ | $C_3H_7$ | H | 181-182 | 54 |
| 23 | Cl | $CH_2COOCH_3$ | $C_4H_9$ | H | 174-177 | 43 |
| 24 | Cl | $CH_2CONHNH_2$ | $C_2H_5$ | H | 206-207 | 55 |
| 25 | Cl | $CH_2CONHNH_2$ | $C_3H_7$ | H | 202-204 | 61 |
| 26 | Cl | $CH_2CONHNH_2$ | $C_4H_9$ | H | 207-209 | 66 |
| 27 | $OCF_3$ | H | $C_2H_5$ | H | 219-222 | 66 |
| 28 | $OCF_3$ | H | $C_3H_7$ | H | 228-229 | 73 |
| 29 | $OCF_3$ | H | $C_4H_9$ | H | 197-199 | 67 |
| 30 | $OCF_3$ | H | $(CH_2)_2OH$ | H | 227-229 | 71 |
| 31 | $OCF_3$ | H | $(CH_2)_2OCH_3$ | H | 211-213 | 46 |
| 32 | $OCF_3$ | H | $H_2C$—△ | H | 242-245 | 48 |
| 33 | $OCF_3$ | $CH_2COCH_3$ | $C_2H_5$ | H | 177-178 | 60 |
| 34 | $OCF_3$ | $CH_2COCH_3$ | $C_3H_7$ | H | 171-174 | 67 |
| 35 | $OCF_3$ | $CH_2COCH_3$ | $C_4H_9$ | H | 165-167 | 53 |
| 36 | $OCF_3$ | $CH_2COOCH_3$ | $C_2H_5$ | H | 187-189 | 57 |
| 37 | $OCF_3$ | $CH_2COOCH_3$ | $C_3H_7$ | H | 185-186 | 56 |
| 38 | $OCF_3$ | $CH_2COOCH_3$ | $C_4H_9$ | H | 180-182 | 44 |
| 39 | $OCF_3$ | $CH_2CONHNH_2$ | $C_2H_5$ | H | 207-208 | 56 |
| 40 | $OCF_3$ | $CH_2CONHNH_2$ | $C_3H_7$ | H | 212-214 | 64 |
| 41 | $OCF_3$ | $CH_2CONHNH_2$ | $C_4H_9$ | H | 217-219 | 68 |
| 42 | $NO_2$ | H | $(CH_2)_2OCH_3$ | H | 215-218 | 45 |
| 43 | $NO_2$ | H | $H_2C$—△ | H | 232-235 | 45 |
| 44 | $NO_2$ | $CH_2COCH_3$ | $C_2H_5$ | H | 176-179 | 60 |
| 45 | $NO_2$ | $CH_2COCH_3$ | $C_3H_7$ | H | 180-182 | 63 |
| 46 | $NO_2$ | $CH_2COCH_3$ | $C_4H_9$ | H | 166-167 | 52 |
| 47 | $NO_2$ | $CH_2COOCH_3$ | $C_2H_5$ | H | 188-189 | 57 |
| 48 | $NO_2$ | $CH_2COOCH_3$ | $C_3H_7$ | H | 214-215 | 65 |
| 49 | $NO_2$ | $CH_2COOCH_3$ | $C_4H_9$ | H | 184-187 | 47 |
| 50 | $NO_2$ | $CH_2CONHNH_2$ | $C_2H_5$ | H | 226-227 | 55 |
| 51 | $NO_2$ | $CH_2CONHNH_2$ | $C_3H_7$ | H | 222-224 | 61 |
| 52 | $NO_2$ | $CH_2CONHNH_2$ | $C_4H_9$ | H | 227-229 | 65 |
| 53 | $NO_2$ | H | $C_2H_5$ | Cl | 221-223 | 52 |
| 54 | $NO_2$ | H | $C_3H_7$ | Cl | 225-226 | 61 |
| 55 | $NO_2$ | H | $C_4H_9$ | Cl | 195-197 | 68 |
| 56 | $NO_2$ | H | $(CH_2)_2OH$ | Cl | 222-224 | 71 |
| 57 | $NO_2$ | H | $(CH_2)_2OCH_3$ | Cl | 220-222 | 46 |
| 58 | $NO_2$ | H | $H_2C$—△ | Cl | 232-235 | 55 |
| 59 | $NO_2$ | $CH_2COCH_3$ | $C_2H_5$ | Cl | 182-183 | 65 |
| 60 | $NO_2$ | $CH_2COCH_3$ | $C_3H_7$ | Cl | 187-189 | 61 |
| 61 | $NO_2$ | $CH_2COCH_3$ | $C_4H_9$ | Cl | 185-187 | 56 |
| 62 | $NO_2$ | $CH_2COOCH_3$ | $C_2H_5$ | Cl | 203-205 | 58 |
| 63 | $NO_2$ | $CH_2COOCH_3$ | $C_3H_7$ | Cl | 212-215 | 61 |
| 64 | $NO_2$ | $CH_2COOCH_3$ | $C_4H_9$ | Cl | 214-217 | 43 |
| 65 | $NO_2$ | $CH_2CONHNH_2$ | $C_2H_5$ | Cl | 226-228 | 59 |
| 66 | $NO_2$ | $CH_2CONHNH_2$ | $C_3H_7$ | Cl | 222-224 | 67 |
| 67 | $NO_2$ | $CH_2CONHNH_2$ | $C_4H_9$ | Cl | 227-229 | 71 |
| 68 | $NO_2$ | H | $C_2H_5$ | F | 224-225 | 57 |
| 69 | $NO_2$ | H | $C_3H_7$ | F | 224-226 | 62 |
| 70 | $NO_2$ | H | $C_4H_9$ | F | 195-198 | 67 |
| 71 | $NO_2$ | H | $(CH_2)_2OH$ | F | 221-222 | 72 |
| 72 | $NO_2$ | H | $(CH_2)_2OCH_3$ | F | 208-210 | 43 |
| 73 | $NO_2$ | H | $H_2C$—△ | F | 222-225 | 45 |
| 74 | $NO_2$ | $CH_2COCH_3$ | $C_2H_5$ | F | 192-193 | 62 |
| 75 | $NO_2$ | $CH_2COCH_3$ | $C_3H_7$ | F | 197-199 | 66 |
| 76 | $NO_2$ | $CH_2COCH_3$ | $C_4H_9$ | F | 195-197 | 55 |
| 77 | $NO_2$ | $CH_2COOCH_3$ | $C_2H_5$ | F | 223-225 | 53 |
| 78 | $NO_2$ | $CH_2COOCH_3$ | $C_3H_7$ | F | 221-222 | 59 |
| 79 | $NO_2$ | $CH_2COOCH_3$ | $C_4H_9$ | F | 214-217 | 62 |
| 80 | $NO_2$ | $CH_2CONHNH_2$ | $C_2H_5$ | F | 210-212 | 53 |
| 81 | $NO_2$ | $CH_2CONHNH_2$ | $C_3H_7$ | F | 208-209 | 63 |
| 82 | $NO_2$ | $CH_2CONHNH_2$ | $C_4H_9$ | F | 212-214 | 65 |

TABLE 2

List of 1-substituted 3-arylamino-1,3-dihydro-2H-benzo[e][1,4]diazepin-2-ones

| No | R¹ | R² | R⁴ | R⁵ | Melting point, °C. | Yield, % |
|---|---|---|---|---|---|---|
| 83 | Br | H | F | 2-COCH₃ | 227-229 | 74 |
| 84 | Br | H | F | 3-COCH₃ | 215-219 | 66 |
| 85 | Br | H | F | 4-COCH₃ | 244-249 | 65 |
| 86 | Br | CH₂COCH₃ | F | 2-COCH₃ | 185-187 | 53 |
| 87 | Br | CH₂COCH₃ | F | 3-COCH₃ | 175-178 | 49 |
| 88 | Br | CH₂COCH₃ | F | 4-COCH₃ | 167-169 | 53 |
| 89 | Br | CH₂COOCH₃ | F | 2-COCH₃ | 178-180 | 57 |
| 90 | Br | CH₂COOCH₃ | F | 3-COCH₃ | 168-172 | 60 |
| 91 | Br | CH₂COOCH₃ | F | 4-COCH₃ | 178-180 | 60 |
| 92 | Br | H | F | 2-Cl | 225-226 | 70 |
| 93 | Br | H | F | 3-Cl | 212-215 | 62 |
| 94 | Br | H | F | 4-Cl | 234-239 | 61 |
| 95 | Br | CH₂COCH₃ | F | 2-Cl | 181-183 | 56 |
| 96 | Br | CH₂COCH₃ | F | 3-Cl | 175-178 | 55 |
| 97 | Br | CH₂COCH₃ | F | 4-Cl | 177-179 | 58 |
| 98 | Br | CH₂COOCH₃ | F | 2-Cl | 198-200 | 57 |
| 99 | Br | CH₂COOCH₃ | F | 3-Cl | 178-180 | 64 |
| 100 | Br | CH₂COOCH₃ | F | 4-Cl | 184-186 | 55 |
| 101 | Br | H | F | 2-F | 225-226 | 70 |
| 102 | Br | H | F | 3-F | 212-215 | 62 |
| 103 | Br | H | F | 4-F | 234-239 | 61 |
| 104 | Br | CH₂COCH₃ | F | 2-F | 181-183 | 56 |
| 105 | Br | CH₂COCH₃ | F | 3-F | 175-178 | 55 |
| 106 | Br | CH₂COCH₃ | F | 4-F | 177-179 | 58 |
| 107 | Br | CH₂COOCH₃ | F | 2-F | 198-200 | 57 |
| 108 | Br | CH₂COOCH₃ | F | 3-F | 178-180 | 64 |
| 109 | Br | CH₂COOCH₃ | F | 4-F | 184-186 | 55 |
| 110 | Br | H | F | 2-Br | 225-226 | 70 |
| 111 | Br | H | F | 3-Br | 212-215 | 62 |
| 112 | Br | H | F | 4-Br | 234-239 | 61 |
| 113 | Br | CH₂COCH₃ | F | 2-Br | 181-183 | 56 |
| 114 | Br | CH₂COCH₃ | F | 3-Br | 175-178 | 55 |
| 115 | Br | CH₂COCH₃ | F | 4-Br | 177-179 | 58 |
| 116 | Br | CH₂COOCH₃ | F | 2-Br | 198-200 | 57 |
| 117 | Br | CH₂COOCH₃ | F | 3-Br | 178-180 | 64 |
| 118 | Br | CH₂COOCH₃ | F | 4-Br | 184-186 | 55 |
| 119 | Br | H | F | 2-NO₂ | 222-224 | 44 |
| 120 | Br | H | F | 3-NO₂ | 225-227 | 65 |
| 121 | Br | H | F | 4-NO₂ | 222-225 | 67 |
| 122 | Br | CH₂COCH₃ | F | 2-NO₂ | 232-234 | 46 |
| 123 | Br | CH₂COCH₃ | F | 3-NO₂ | 235-237 | 62 |
| 124 | Br | CH₂COCH₃ | F | 4-NO₂ | 232-235 | 64 |
| 125 | Br | CH₂COOCH₃ | F | 2-NO₂ | 242-244 | 65 |
| 126 | Br | CH₂COOCH₃ | F | 3-NO₂ | 223-226 | 51 |
| 127 | Br | CH₂COOCH₃ | F | 4-NO₂ | 240-244 | 67 |
| 128 | Br | H | F | 2-CF₃ | 225-226 | 70 |
| 129 | Br | H | F | 3-CF₃ | 212-215 | 62 |
| 130 | Br | H | F | 4-CF₃ | 234-239 | 61 |
| 131 | Br | CH₂COCH₃ | F | 2-CF₃ | 181-183 | 56 |
| 132 | Br | CH₂COCH₃ | F | 3-CF₃ | 175-178 | 55 |
| 133 | Br | CH₂COCH₃ | F | 4-CF₃ | 177-179 | 58 |
| 134 | Br | CH₂COOCH₃ | F | 2-CF₃ | 198-200 | 57 |
| 135 | Br | CH₂COOCH₃ | F | 3-CF₃ | 178-180 | 64 |
| 136 | Br | CH₂COOCH₃ | F | 4-CF₃ | 184-186 | 55 |
| 137 | Cl | H | H | 2-COCH₃ | 225-226 | 70 |
| 138 | Cl | H | H | 3-COCH₃ | 212-215 | 62 |
| 139 | Cl | H | H | 4-COCH₃ | 234-239 | 61 |
| 140 | Cl | CH₂COCH₃ | H | 2-COCH₃ | 181-183 | 56 |
| 141 | Cl | CH₂COCH₃ | H | 3-COCH₃ | 175-178 | 55 |
| 142 | Cl | CH₂COCH₃ | H | 4-COCH₃ | 177-179 | 58 |
| 143 | Cl | CH₂COOCH₃ | H | 2-COCH₃ | 198-200 | 57 |
| 144 | Cl | CH₂COOCH₃ | H | 3-COCH₃ | 178-180 | 64 |
| 145 | Cl | CH₂COOCH₃ | H | 4-COCH₃ | 184-186 | 55 |
| 146 | Cl | CH₂COCH₃ | H | 2-Cl | 181-183 | 56 |
| 147 | Cl | CH₂COCH₃ | H | 3-Cl | 175-178 | 55 |
| 148 | Cl | CH₂COCH₃ | H | 4-Cl | 177-179 | 58 |
| 149 | Cl | CH₂COOCH₃ | H | 2-Cl | 198-200 | 57 |
| 150 | Cl | CH₂COOCH₃ | H | 3-Cl | 178-180 | 64 |
| 151 | Cl | CH₂COOCH₃ | H | 4-Cl | 184-186 | 55 |
| 152 | Cl | H | H | 2-F | 225-226 | 70 |
| 153 | Cl | H | H | 3-F | 212-215 | 62 |
| 154 | Cl | H | H | 4-F | 234-239 | 61 |
| 155 | Cl | CH₂COCH₃ | H | 2-F | 181-183 | 56 |
| 156 | Cl | CH₂COCH₃ | H | 3-F | 175-178 | 55 |
| 157 | Cl | CH₂COCH₃ | H | 4-F | 177-179 | 58 |
| 158 | Cl | CH₂COOCH₃ | H | 2-F | 198-200 | 57 |
| 159 | Cl | CH₂COOCH₃ | H | 3-F | 178-180 | 64 |
| 160 | Cl | CH₂COOCH₃ | H | 4-F | 184-186 | 55 |
| 161 | Cl | H | H | 2-Br | 225-226 | 70 |
| 162 | Cl | H | H | 3-Br | 212-215 | 62 |
| 163 | Cl | H | H | 4-Br | 234-239 | 61 |
| 164 | Cl | CH₂COCH₃ | H | 2-Br | 181-183 | 56 |
| 165 | Cl | CH₂COCH₃ | H | 3-Br | 175-178 | 55 |
| 166 | Cl | CH₂COCH₃ | H | 4-Br | 177-179 | 58 |
| 167 | Cl | CH₂COOCH₃ | H | 2-Br | 198-200 | 57 |
| 168 | Cl | CH₂COOCH₃ | H | 3-Br | 178-180 | 64 |
| 169 | Cl | CH₂COOCH₃ | H | 4-Br | 184-186 | 55 |
| 170 | Cl | CH₂COCH₃ | H | 2-NO₂ | 181-183 | 56 |
| 171 | Cl | CH₂COCH₃ | H | 3-NO₂ | 175-178 | 55 |
| 172 | Cl | CH₂COCH₃ | H | 4-NO₂ | 177-179 | 58 |
| 173 | Cl | CH₂COOCH₃ | H | 2-NO₂ | 198-200 | 57 |
| 174 | Cl | CH₂COOCH₃ | H | 3-NO₂ | 178-180 | 64 |
| 175 | Cl | CH₂COOCH₃ | H | 4-NO₂ | 184-186 | 55 |
| 176 | Cl | H | H | 2-CF₃ | 225-226 | 70 |
| 177 | Cl | H | H | 3-CF₃ | 212-215 | 62 |
| 178 | Cl | H | H | 4-CF₃ | 234-239 | 61 |
| 179 | Cl | CH₂COCH₃ | H | 2-CF₃ | 181-183 | 56 |
| 180 | Cl | CH₂COCH₃ | H | 3-CF₃ | 175-178 | 55 |
| 181 | Cl | CH₂COCH₃ | H | 4-CF₃ | 177-179 | 58 |
| 182 | Cl | CH₂COOCH₃ | H | 2-CF₃ | 198-200 | 57 |
| 183 | Cl | CH₂COOCH₃ | H | 3-CF₃ | 178-180 | 64 |
| 184 | Cl | CH₂COOCH₃ | H | 4-CF₃ | 184-186 | 55 |
| 185 | OCF₃ | H | H | 2-COCH₃ | 225-226 | 70 |
| 186 | OCF₃ | H | H | 3-COCH₃ | 212-215 | 62 |
| 187 | OCF₃ | H | H | 4-COCH₃ | 234-239 | 61 |
| 188 | OCF₃ | CH₂COCH₃ | H | 2-COCH₃ | 181-183 | 56 |
| 189 | OCF₃ | CH₂COCH₃ | H | 3-COCH₃ | 175-178 | 55 |
| 190 | OCF₃ | CH₂COCH₃ | H | 4-COCH₃ | 177-179 | 58 |
| 191 | OCF₃ | CH₂COOCH₃ | H | 2-COCH₃ | 198-200 | 57 |
| 192 | OCF₃ | CH₂COOCH₃ | H | 3-COCH₃ | 178-180 | 64 |
| 193 | OCF₃ | CH₂COOCH₃ | H | 4-COCH₃ | 184-186 | 55 |
| 194 | OCF₃ | H | H | 2-Cl | 225-226 | 70 |
| 195 | OCF₃ | H | H | 3-Cl | 212-215 | 62 |
| 196 | OCF₃ | H | H | 4-Cl | 234-239 | 61 |
| 197 | OCF₃ | CH₂COCH₃ | H | 2-Cl | 181-183 | 56 |
| 198 | OCF₃ | CH₂COCH₃ | H | 3-Cl | 175-178 | 55 |
| 199 | OCF₃ | CH₂COCH₃ | H | 4-Cl | 177-179 | 58 |
| 200 | OCF₃ | CH₂COOCH₃ | H | 2-Cl | 198-200 | 57 |
| 201 | OCF₃ | CH₂COOCH₃ | H | 3-Cl | 178-180 | 64 |
| 202 | OCF₃ | CH₂COOCH₃ | H | 4-Cl | 184-186 | 55 |
| 203 | OCF₃ | H | H | 2-F | 225-226 | 70 |
| 204 | OCF₃ | H | H | 3-F | 212-215 | 62 |
| 205 | OCF₃ | H | H | 4-F | 234-239 | 61 |
| 206 | OCF₃ | CH₂COCH₃ | H | 2-F | 181-183 | 56 |
| 207 | OCF₃ | CH₂COCH₃ | H | 3-F | 175-178 | 55 |
| 208 | OCF₃ | CH₂COCH₃ | H | 4-F | 177-179 | 58 |
| 209 | OCF₃ | CH₂COOCH₃ | H | 2-F | 198-200 | 57 |
| 210 | OCF₃ | CH₂COOCH₃ | H | 3-F | 178-180 | 64 |
| 211 | OCF₃ | CH₂COOCH₃ | H | 4-F | 184-186 | 55 |
| 212 | OCF₃ | H | H | 2-Br | 225-226 | 70 |
| 213 | OCF₃ | H | H | 3-Br | 212-215 | 62 |
| 214 | OCF₃ | H | H | 4-Br | 234-239 | 61 |
| 215 | OCF₃ | CH₂COCH₃ | H | 2-Br | 181-183 | 56 |
| 216 | OCF₃ | CH₂COCH₃ | H | 3-Br | 175-178 | 55 |
| 217 | OCF₃ | CH₂COCH₃ | H | 4-Br | 177-179 | 58 |
| 218 | OCF₃ | CH₂COOCH₃ | H | 2-Br | 198-200 | 57 |
| 219 | OCF₃ | CH₂COOCH₃ | H | 3-Br | 178-180 | 64 |
| 220 | OCF₃ | CH₂COOCH₃ | H | 4-Br | 184-186 | 55 |
| 221 | OCF₃ | H | H | 2-NO₂ | 225-226 | 70 |
| 222 | OCF₃ | H | H | 3-NO₂ | 212-215 | 62 |
| 223 | OCF₃ | H | H | 4-NO₂ | 234-239 | 61 |
| 224 | OCF₃ | CH₂COCH₃ | H | 2-NO₂ | 181-183 | 56 |
| 225 | OCF₃ | CH₂COCH₃ | H | 3-NO₂ | 175-178 | 55 |
| 226 | OCF₃ | CH₂COCH₃ | H | 4-NO₂ | 177-179 | 58 |
| 227 | OCF₃ | CH₂COOCH₃ | H | 2-NO₂ | 198-200 | 57 |
| 228 | OCF₃ | CH₂COOCH₃ | H | 3-NO₂ | 178-180 | 64 |

TABLE 2-continued

List of 1-substituted 3-arylamino-1,3-dihydro-2H-benzo[e][1,4]diazepin-2-ones

| No | R¹ | R² | R⁴ | R⁵ | Melting point, °C. | Yield, % |
|---|---|---|---|---|---|---|
| 229 | OCF₃ | CH₂COOCH₃ | H | 4-NO₂ | 184-186 | 55 |
| 230 | OCF₃ | H | H | 2-CF₃ | 225-226 | 70 |
| 231 | OCF₃ | H | H | 3-CF₃ | 212-215 | 62 |
| 232 | OCF₃ | H | H | 4-CF₃ | 234-239 | 61 |
| 233 | OCF₃ | CH₂COCH₃ | H | 2-CF₃ | 181-183 | 56 |
| 234 | OCF₃ | CH₂COCH₃ | H | 3-CF₃ | 175-178 | 55 |
| 235 | OCF₃ | CH₂COCH₃ | H | 4-CF₃ | 177-179 | 58 |
| 236 | OCF₃ | CH₂COOCH₃ | H | 2-CF₃ | 198-200 | 57 |
| 237 | OCF₃ | CH₂COOCH₃ | H | 3-CF₃ | 178-180 | 64 |
| 238 | OCF₃ | CH₂COOCH₃ | H | 4-CF₃ | 184-186 | 55 |
| 239 | NO₂ | H | H | 2-COCH₃ | 225-226 | 70 |
| 240 | NO₂ | H | H | 3-COCH₃ | 212-215 | 62 |
| 241 | NO₂ | H | H | 4-COCH₃ | 234-239 | 61 |
| 242 | NO₂ | CH₂COCH₃ | H | 2-COCH₃ | 181-183 | 56 |
| 243 | NO₂ | CH₂COCH₃ | H | 3-COCH₃ | 175-178 | 55 |
| 244 | NO₂ | CH₂COCH₃ | H | 4-COCH₃ | 177-179 | 58 |
| 245 | NO₂ | CH₂COOCH₃ | H | 2-COCH₃ | 198-200 | 57 |
| 246 | NO₂ | CH₂COOCH₃ | H | 3-COCH₃ | 178-180 | 64 |
| 247 | NO₂ | CH₂COOCH₃ | H | 4-COCH₃ | 184-186 | 55 |
| 248 | NO₂ | H | H | 2-Cl | 225-226 | 70 |
| 249 | NO₂ | H | H | 3-Cl | 212-215 | 62 |
| 250 | NO₂ | H | H | 4-Cl | 234-239 | 61 |
| 251 | NO₂ | CH₂COCH₃ | H | 2-Cl | 181-183 | 56 |
| 252 | NO₂ | CH₂COCH₃ | H | 3-Cl | 175-178 | 55 |
| 253 | NO₂ | CH₂COCH₃ | H | 4-Cl | 177-179 | 58 |
| 254 | NO₂ | CH₂COOCH₃ | H | 2-Cl | 198-200 | 57 |
| 255 | NO₂ | CH₂COOCH₃ | H | 3-Cl | 178-180 | 64 |
| 256 | NO₂ | CH₂COOCH₃ | H | 4-Cl | 184-186 | 55 |
| 257 | NO₂ | H | H | 2-F | 225-226 | 70 |
| 258 | NO₂ | H | H | 3-F | 212-215 | 62 |
| 259 | NO₂ | H | H | 4-F | 234-239 | 61 |
| 260 | NO₂ | CH₂COCH₃ | H | 2-F | 181-183 | 56 |
| 261 | NO₂ | CH₂COCH₃ | H | 3-F | 175-178 | 55 |
| 262 | NO₂ | CH₂COCH₃ | H | 4-F | 177-179 | 58 |
| 263 | NO₂ | CH₂COOCH₃ | H | 2-F | 198-200 | 57 |
| 264 | NO₂ | CH₂COOCH₃ | H | 3-F | 178-180 | 64 |
| 265 | NO₂ | CH₂COOCH₃ | H | 4-F | 184-186 | 55 |
| 266 | NO₂ | H | H | 2-Br | 225-226 | 70 |
| 267 | NO₂ | H | H | 3-Br | 212-215 | 62 |
| 268 | NO₂ | H | H | 4-Br | 234-239 | 61 |
| 269 | NO₂ | CH₂COCH₃ | H | 2-Br | 181-183 | 56 |
| 270 | NO₂ | CH₂COCH₃ | H | 3-Br | 175-178 | 55 |
| 271 | NO₂ | CH₂COCH₃ | H | 4-Br | 177-179 | 58 |
| 272 | NO₂ | CH₂COOCH₃ | H | 2-Br | 198-200 | 57 |
| 273 | NO₂ | CH₂COOCH₃ | H | 3-Br | 178-180 | 64 |
| 274 | NO₂ | CH₂COOCH₃ | H | 4-Br | 184-186 | 55 |
| 275 | NO₂ | H | H | 2-NO₂ | 225-227 | 64 |
| 276 | NO₂ | H | H | 3-NO₂ | 212-215 | 62 |
| 277 | NO₂ | H | H | 4-NO₂ | 234-239 | 61 |
| 278 | NO₂ | CH₂COCH₃ | H | 2-NO₂ | 181-183 | 56 |
| 279 | NO₂ | CH₂COCH₃ | H | 3-NO₂ | 175-178 | 55 |
| 280 | NO₂ | CH₂COCH₃ | H | 4-NO₂ | 177-179 | 58 |
| 281 | NO₂ | CH₂COOCH₃ | H | 2-NO₂ | 218-220 | 61 |
| 282 | NO₂ | CH₂COOCH₃ | H | 3-NO₂ | 178-180 | 64 |
| 283 | NO₂ | CH₂COOCH₃ | H | 4-NO₂ | 184-186 | 55 |
| 284 | NO₂ | H | H | 2-CF₃ | 225-227 | 64 |
| 285 | NO₂ | H | H | 3-CF₃ | 212-215 | 62 |
| 286 | NO₂ | H | H | 4-CF₃ | 234-239 | 61 |
| 287 | NO₂ | CH₂COCH₃ | H | 2-CF₃ | 181-183 | 56 |
| 288 | NO₂ | CH₂COCH₃ | H | 3-CF₃ | 175-178 | 55 |
| 289 | NO₂ | CH₂COCH₃ | H | 4-CF₃ | 177-179 | 58 |
| 290 | NO₂ | CH₂COOCH₃ | H | 2-CF₃ | 218-220 | 61 |
| 291 | NO₂ | CH₂COOCH₃ | H | 3-CF₃ | 178-180 | 64 |
| 292 | NO₂ | CH₂COOCH₃ | H | 4-CF₃ | 184-186 | 55 |
| 293 | NO₂ | H | Cl | 2-COCH₃ | 225-227 | 64 |
| 294 | NO₂ | H | Cl | 3-COCH₃ | 212-215 | 62 |
| 295 | NO₂ | H | Cl | 4-COCH₃ | 234-239 | 61 |
| 296 | NO₂ | CH₂COCH₃ | Cl | 2-COCH₃ | 181-183 | 56 |
| 297 | NO₂ | CH₂COCH₃ | Cl | 3-COCH₃ | 175-178 | 55 |
| 298 | NO₂ | CH₂COCH₃ | Cl | 4-COCH₃ | 177-179 | 58 |
| 299 | NO₂ | CH₂COOCH₃ | Cl | 2-COCH₃ | 218-220 | 61 |
| 300 | NO₂ | CH₂COOCH₃ | Cl | 3-COCH₃ | 178-180 | 64 |
| 301 | NO₂ | CH₂COOCH₃ | Cl | 4-COCH₃ | 184-186 | 55 |
| 302 | NO₂ | H | Cl | 2-Cl | 225-227 | 64 |
| 303 | NO₂ | H | Cl | 3-Cl | 212-215 | 62 |
| 304 | NO₂ | H | Cl | 4-Cl | 234-239 | 61 |
| 305 | NO₂ | CH₂COCH₃ | Cl | 2-Cl | 181-183 | 56 |
| 306 | NO₂ | CH₂COCH₃ | Cl | 3-Cl | 175-178 | 55 |
| 307 | NO₂ | CH₂COCH₃ | Cl | 4-Cl | 177-179 | 58 |
| 308 | NO₂ | CH₂COOCH₃ | Cl | 2-Cl | 218-220 | 61 |
| 309 | NO₂ | CH₂COOCH₃ | Cl | 3-Cl | 178-180 | 64 |
| 310 | NO₂ | CH₂COOCH₃ | Cl | 4-Cl | 184-186 | 55 |
| 311 | NO₂ | H | Cl | 2-F | 225-227 | 64 |
| 312 | NO₂ | H | Cl | 3-F | 212-215 | 62 |
| 313 | NO₂ | H | Cl | 4-F | 234-239 | 61 |
| 314 | NO₂ | CH₂COCH₃ | Cl | 2-F | 181-183 | 56 |
| 315 | NO₂ | CH₂COCH₃ | Cl | 3-F | 175-178 | 55 |
| 316 | NO₂ | CH₂COCH₃ | Cl | 4-F | 177-179 | 58 |
| 317 | NO₂ | CH₂COOCH₃ | Cl | 2-F | 218-220 | 61 |
| 318 | NO₂ | CH₂COOCH₃ | Cl | 3-F | 178-180 | 64 |
| 319 | NO₂ | CH₂COOCH₃ | Cl | 4-F | 184-186 | 55 |
| 320 | NO₂ | H | Cl | 2-Br | 225-227 | 64 |
| 321 | NO₂ | H | Cl | 3-Br | 212-215 | 62 |
| 322 | NO₂ | H | Cl | 4-Br | 234-239 | 61 |
| 323 | NO₂ | CH₂COCH₃ | Cl | 2-Br | 181-183 | 56 |
| 324 | NO₂ | CH₂COCH₃ | Cl | 3-Br | 175-178 | 55 |
| 325 | NO₂ | CH₂COCH₃ | Cl | 4-Br | 177-179 | 58 |
| 326 | NO₂ | CH₂COOCH₃ | Cl | 2-Br | 218-220 | 61 |
| 327 | NO₂ | CH₂COOCH₃ | Cl | 3-Br | 178-180 | 64 |
| 328 | NO₂ | CH₂COOCH₃ | Cl | 4-Br | 184-186 | 55 |
| 329 | NO₂ | H | Cl | 2-NO₂ | 225-227 | 64 |
| 330 | NO₂ | H | Cl | 3-NO₂ | 212-215 | 62 |
| 331 | NO₂ | H | Cl | 4-NO₂ | 234-239 | 61 |
| 332 | NO₂ | CH₂COCH₃ | Cl | 2-NO₂ | 181-183 | 56 |
| 333 | NO₂ | CH₂COCH₃ | Cl | 3-NO₂ | 175-178 | 55 |
| 334 | NO₂ | CH₂COCH₃ | Cl | 4-NO₂ | 177-179 | 58 |
| 335 | NO₂ | CH₂COOCH₃ | Cl | 2-NO₂ | 218-220 | 61 |
| 336 | NO₂ | CH₂COOCH₃ | Cl | 3-NO₂ | 178-180 | 64 |
| 337 | NO₂ | CH₂COOCH₃ | Cl | 4-NO₂ | 184-186 | 55 |
| 338 | NO₂ | H | Cl | 2-CF₃ | 225-227 | 64 |
| 339 | NO₂ | H | Cl | 3-CF₃ | 212-215 | 62 |
| 340 | NO₂ | H | Cl | 4-CF₃ | 234-239 | 61 |
| 341 | NO₂ | CH₂COCH₃ | Cl | 2-CF₃ | 181-183 | 56 |
| 342 | NO₂ | CH₂COCH₃ | Cl | 3-CF₃ | 175-178 | 55 |
| 343 | NO₂ | CH₂COCH₃ | Cl | 4-CF₃ | 177-179 | 58 |
| 344 | NO₂ | CH₂COOCH₃ | Cl | 2-CF₃ | 218-220 | 61 |
| 345 | NO₂ | CH₂COOCH₃ | Cl | 3-CF₃ | 178-180 | 64 |
| 346 | NO₂ | CH₂COOCH₃ | Cl | 4-CF₃ | 184-186 | 55 |
| 347 | NO₂ | H | F | 2-COCH₃ | 225-227 | 64 |
| 348 | NO₂ | H | F | 3-COCH₃ | 212-215 | 62 |
| 349 | NO₂ | H | F | 4-COCH₃ | 234-239 | 61 |
| 350 | NO₂ | CH₂COCH₃ | F | 2-COCH₃ | 181-183 | 56 |
| 351 | NO₂ | CH₂COCH₃ | F | 3-COCH₃ | 175-178 | 55 |
| 352 | NO₂ | CH₂COCH₃ | F | 4-COCH₃ | 177-179 | 58 |
| 353 | NO₂ | CH₂COOCH₃ | F | 2-COCH₃ | 218-220 | 61 |
| 354 | NO₂ | CH₂COOCH₃ | F | 3-COCH₃ | 178-180 | 64 |
| 355 | NO₂ | CH₂COOCH₃ | F | 4-COCH₃ | 184-186 | 55 |
| 356 | NO₂ | H | F | 2-Cl | 225-227 | 64 |
| 357 | NO₂ | H | F | 3-Cl | 212-215 | 62 |
| 358 | NO₂ | H | F | 4-Cl | 234-239 | 61 |
| 359 | NO₂ | CH₂COCH₃ | F | 2-Cl | 181-183 | 56 |
| 360 | NO₂ | CH₂COCH₃ | F | 3-Cl | 175-178 | 55 |
| 361 | NO₂ | CH₂COCH₃ | F | 4-Cl | 177-179 | 58 |
| 362 | NO₂ | CH₂COOCH₃ | F | 2-Cl | 218-220 | 61 |
| 363 | NO₂ | CH₂COOCH₃ | F | 3-Cl | 178-180 | 64 |
| 364 | NO₂ | CH₂COOCH₃ | F | 4-Cl | 184-186 | 55 |
| 365 | NO₂ | H | F | 2-F | 225-227 | 64 |
| 366 | NO₂ | H | F | 3-F | 212-215 | 62 |
| 367 | NO₂ | H | F | 4-F | 234-239 | 61 |
| 368 | NO₂ | CH₂COCH₃ | F | 2-F | 181-183 | 56 |
| 369 | NO₂ | CH₂COCH₃ | F | 3-F | 175-178 | 55 |
| 370 | NO₂ | CH₂COCH₃ | F | 4-F | 177-179 | 58 |
| 371 | NO₂ | CH₂COOCH₃ | F | 2-F | 218-220 | 61 |
| 372 | NO₂ | CH₂COOCH₃ | F | 3-F | 178-180 | 64 |
| 373 | NO₂ | CH₂COOCH₃ | F | 4-F | 184-186 | 55 |
| 374 | NO₂ | H | F | 2-Br | 225-227 | 64 |

TABLE 2-continued

List of 1-substituted 3-arylamino-1,3-dihydro-2H-benzo[e][1,4]diazepin-2-ones

| No | $R^1$ | $R^2$ | $R^4$ | $R^5$ | Melting point, °C. | Yield, % |
|---|---|---|---|---|---|---|
| 375 | $NO_2$ | H | F | 3-Br | 212-215 | 62 |
| 376 | $NO_2$ | H | F | 4-Br | 234-239 | 61 |
| 377 | $NO_2$ | $CH_2COCH_3$ | F | 2-Br | 181-183 | 56 |
| 378 | $NO_2$ | $CH_2COCH_3$ | F | 3-Br | 175-178 | 55 |
| 379 | $NO_2$ | $CH_2COCH_3$ | F | 4-Br | 177-179 | 58 |
| 380 | $NO_2$ | $CH_2COOCH_3$ | F | 2-Br | 218-220 | 61 |
| 381 | $NO_2$ | $CH_2COOCH_3$ | F | 3-Br | 178-180 | 64 |
| 382 | $NO_2$ | $CH_2COOCH_3$ | F | 4-Br | 184-186 | 55 |
| 383 | $NO_2$ | H | F | 2-$NO_2$ | 225-227 | 64 |
| 384 | $NO_2$ | H | F | 3-$NO_2$ | 212-215 | 62 |
| 385 | $NO_2$ | H | F | 4-$NO_2$ | 234-239 | 61 |
| 386 | $NO_2$ | $CH_2COCH_3$ | F | 2-$NO_2$ | 181-183 | 56 |
| 387 | $NO_2$ | $CH_2COCH_3$ | F | 3-$NO_2$ | 175-178 | 55 |
| 388 | $NO_2$ | $CH_2COCH_3$ | F | 4-$NO_2$ | 177-179 | 58 |
| 389 | $NO_2$ | $CH_2COOCH_3$ | F | 2-$NO2$ | 218-220 | 61 |
| 390 | $NO_2$ | $CH_2COOCH_3$ | F | 3-$NO_2$ | 178-180 | 64 |
| 391 | $NO_2$ | $CH_2COOCH_3$ | F | 4-$NO_2$ | 184-186 | 55 |
| 392 | $NO_2$ | H | F | 2-$CF_3$ | 225-227 | 64 |
| 393 | $NO_2$ | H | F | 3-$CF_3$ | 212-215 | 62 |
| 394 | $NO_2$ | H | F | 4-$CF_3$ | 234-239 | 61 |
| 395 | $NO_2$ | $CH_2COCH_3$ | F | 2-$CF_3$ | 181-183 | 56 |
| 396 | $NO_2$ | $CH_2COCH_3$ | F | 3-$CF_3$ | 175-178 | 55 |
| 397 | $NO_2$ | $CH_2COCH_3$ | F | 4-$CF_3$ | 177-179 | 58 |
| 398 | $NO_2$ | $CH_2COOCH_3$ | F | 2-$CF_3$ | 218-220 | 61 |
| 399 | $NO_2$ | $CH_2COOCH_3$ | F | 3-$CF_3$ | 178-180 | 64 |
| 400 | $NO_2$ | $CH_2COOCH_3$ | F | 4-$CF_3$ | 184-186 | 55 |

TABLE 3

Affinity of 3-alcoxy-1,3-dihydro-2H-benzo[e][1,4]diazepin-2-ones (Ia) to central and peripheral benzodiazepine receptors

| No | $R^1$ | $R^2$ | Alk | $R^4$ | CBR, % | PBR, % |
|---|---|---|---|---|---|---|
| 2 | Br | H | $C_3H_7$ | F | 85 | 5 |
| 3 | Br | H | $C_4H_9$ | F | 88 | 8 |
| 4 | Br | H | $(CH_2)_2OH$ | F | 91 | 8 |
| 5 | Br | H | $(CH_2)_2OCH_3$ | F | 90 | 10 |
| 6 | Br | H | $H_2C$-cyclopropyl | F | 89 | 15 |
| 16 | Cl | H | $(CH_2)_2OCH_3$ | H | 88 | 15 |
| 17 | Cl | H | $H_2C$-cyclopropyl | H | 79 | 14 |
| 18 | Cl | $CH_2COOCH_3$ | $C_2H_5$ | H | 80 | 18 |
| 19 | Cl | $CH_2COOCH_3$ | $C_3H_7$ | H | 85 | 16 |
| 20 | Cl | $CH_2COOCH_3$ | $C_4H_9$ | H | 52 | 15 |
| 27 | $OCF_3$ | H | $C_2H_5$ | H | 56 | 16 |
| 28 | $OCF_3$ | H | $C_3H_7$ | H | 60 | 18 |
| 29 | $OCF_3$ | H | $C_4H_9$ | H | 61 | 15 |
| 30 | $OCF_3$ | H | $(CH_2)_2OH$ | H | 65 | 16 |
| 44 | $NO_2$ | $CH_2COOCH_3$ | $C_2H_5$ | H | 14 | 22 |
| 45 | $NO_2$ | $CH_2COOCH_3$ | $C_3H_7$ | H | 12 | 25 |
| 46 | $NO_2$ | $CH_2COOCH_3$ | $C_4H_9$ | H | 11 | 20 |
| 53 | $NO_2$ | H | $C_2H_5$ | Cl | 85 | 15 |
| 54 | $NO_2$ | H | $C_3H_7$ | Cl | 88 | 16 |
| 55 | $NO_2$ | H | $C_4H_9$ | Cl | 87 | 19 |
| 59 | $NO_2$ | $CH_2COOCH_3$ | $C_2H_5$ | Cl | 50 | 18 |
| 60 | $NO_2$ | $CH_2COOCH_3$ | $C_3H_7$ | Cl | 58 | 18 |

TABLE 4

Analgesic activity of 3-alcoxy-1,3-dihydro-2H-benzo[e][1,4]diazepin-2-ones (Ia)

| No | $R^1$ | $R^2$ | Alk | $R^4$ | Writhing inhibition, % of control in 1 mg/kg dose |
|---|---|---|---|---|---|
| 2 | Br | H | $C_3H_7$ | F | 55 |
| 3 | Br | H | $C_4H_9$ | F | 45 |
| 4 | Br | H | $(CH_2)_2OH$ | F | 56 |
| 5 | Br | H | $(CH_2)_2OCH_3$ | F | 52 |
| 6 | Br | H | $H_2C$-cyclopropyl | F | 55 |
| 16 | Cl | H | $(CH2)2OCH_3$ | H | 55 |
| 17 | Cl | H | $H_2C$-cyclopropyl | H | 54 |
| 21 | Cl | $CH_2COOCH_3$ | $C_2H_5$ | H | 62 |
| 22 | Cl | $CH_2COOCH_3$ | $C_3H_7$ | H | 70 |
| 23 | Cl | $CH_2COOCH_3$ | $C_4H_9$ | H | 52 |
| 27 | $OCF_3$ | H | $C_2H_5$ | H | 55 |
| 28 | $OCF_3$ | H | $C_3H_7$ | H | 60 |
| 29 | $OCF_3$ | H | $C_4H_9$ | H | 56 |
| 30 | $OCF_3$ | H | $(CH_2)_2OH$ | H | 50 |
| 44 | $NO_2$ | $CH_2COOCH_3$ | $C_2H_5$ | H | 65 |
| 45 | $NO_2$ | $CH_2COOCH_3$ | $C_3H_7$ | H | 88 |
| 46 | $NO_2$ | $CH_2COOCH_3$ | $C_4H_9$ | H | 55 |
| 59 | $NO_2$ | $CH_2COOCH_3$ | $C_2H_5$ | Cl | 61 |
| 48 | $NO_2$ | $CH_2COOCH_3$ | $C_3H_7$ | Cl | 85 |

TABLE 5

Analgesic activity of 3-arylamino-1,3-dihydro-2H-benzo[e][1,4]diazepin-2-ones (Ib)

| № | $R^1$ | $R^2$ | $R^4$ | $R^5$ | Writhing inhibition, % of control in 1 mg/kg dose |
|---|---|---|---|---|---|
| 89 | Br | $CH_2COOCH_3$ | F | 2-$COCH_3$ | 66 |
| 90 | Br | $CH_2COOCH_3$ | F | 3-$COCH_3$ | 68 |
| 91 | Br | $CH_2COOCH_3$ | F | 4-$COCH_3$ | 62 |
| 173 | Cl | $CH_2COOCH_3$ | H | 2-$NO_2$ | 55 |
| 174 | Cl | $CH_2COOCH_3$ | H | 3-$NO_2$ | 58 |
| 175 | Cl | $CH_2COOCH_3$ | H | 4-$NO_2$ | 55 |
| 227 | $OCF_3$ | $CH_2COOCH_3$ | H | 2-$NO_2$ | 60 |
| 228 | $OCF_3$ | $CH_2COOCH_3$ | H | 3-$NO_2$ | 62 |
| 229 | $OCF_3$ | $CH_2COOCH_3$ | H | 4-$NO_2$ | 59 |
| 281 | $NO_2$ | $CH_2COOCH_3$ | H | 2-$NO_2$ | 61 |
| 282 | $NO_2$ | $CH_2COOCH_3$ | H | 3-$NO_2$ | 59 |
| 283 | $NO_2$ | $CH_2COOCH_3$ | H | 4-$NO_2$ | 54 |
| 317 | $NO_2$ | $CH_2COOCH_3$ | Cl | 2-F | 63 |
| 318 | $NO_2$ | $CH_2COOCH_3$ | Cl | 3-F | 65 |
| 319 | $NO_2$ | $CH_2COOCH_3$ | Cl | 4-F | 61 |
| 326 | $NO_2$ | $CH_2COOCH_3$ | Cl | 2-Br | 62 |
| 327 | $NO_2$ | $CH_2COOCH_3$ | Cl | 3-Br | 70 |
| 328 | $NO_2$ | $CH_2COOCH_3$ | Cl | 4-Br | 69 |
| 362 | $NO_2$ | $CH_2COOCH_3$ | F | 2-Cl | 65 |
| 363 | $NO_2$ | $CH_2COOCH_3$ | F | 3-Cl | 70 |
| 364 | $NO_2$ | $CH_2COOCH_3$ | F | 4-Cl | 64 |
| 398 | $NO_2$ | $CH_2COOCH_3$ | F | 2-$CF_3$ | 68 |
| 399 | $NO_2$ | $CH_2COOCH_3$ | F | 3-$CF_3$ | 70 |
| 400 | $NO_2$ | $CH_2COOCH_3$ | F | 4-$CF_3$ | 60 |

TABLE 6

Effect of 3-arylamino-1,3-dihydro-2H-benzo[e][1,4] diazepin-2-ones (Ib) on food consumption by rats

| No | $R^1$ | $R^2$ | $R^4$ | $R^5$ | Dose mg/kg | Amount of consumed liquid food during 30 min in ml | % of control |
|----|-------|-------|-------|-------|------------|---------------------------------------------------|--------------|
| 152 | Cl | H | H | 2-F | 0,1 | 3,5 ± 1,3 | 47 |
| 161 | Cl | H | H | 2-Br | 0,1 | 5,5 ± 2,4 | 74 |
| 162 | Cl | H | H | 3-Br | 0,1 | 5,1 ± 2,2 | 69 |
| 163 | Cl | H | H | 4-Br | 0,1 | 6,8 ± 2,7 | 92 |
| 194 | $OCF_3$ | H | H | 2-Cl | 0,1 | 3,5 ± 2,3 | 47 |
| 195 | $OCF_3$ | H | H | 3-Cl | 0,1 | 5,7 ± 2,2 | 77 |
| 196 | $OCF_3$ | H | H | 4-Cl | 0,1 | 6,5 ± 3,2 | 88 |
| 248 | $NO_2$ | H | H | 2-Cl | 0,1 | 3,1 ± 2,4 | 41 |
| 249 | $NO_2$ | H | H | 3-Cl | 0,1 | 5,1 ± 2,2 | 69 |
| 250 | $NO_2$ | H | H | 4-Cl | 0,1 | 6,3 ± 3,2 | 85 |
| 320 | $NO_2$ | H | Cl | 2-Br | 0,1 | 6,5 ± 3,4 | 88 |
| 321 | $NO_2$ | H | Cl | 3-Br | 0,1 | 6,1 ± 3,2 | 82 |
| 322 | $NO_2$ | H | Cl | 4-Br | 0,1 | 7,8 ± 2,7 | 105 |
| 347 | $NO_2$ | H | F | 2-$COCH_3$ | 0,1 | 6,5 ± 2,7 | 105 |
| 348 | $NO_2$ | H | F | 3-$COCH_3$ | 0,1 | 21,4 ± 4,9 | 284 |
| 349 | $NO_2$ | H | F | 4-$COCH_3$ | 0,1 | 14 ± 1,8 | 189 |
| 356 | $NO_2$ | H | F | 2-Cl | 0,1 | 2,9 ± 2,1* | 39 |
| 357 | $NO_2$ | H | F | 3-Cl | 0,1 | 5,9 ± 2,2 | 80 |
| 358 | $NO_2$ | H | F | 4-Cl | 0,1 | 6,7 ± 3,2 | 90 |
| Control | | | | | | 7,4 ± 4,4 | 100 |
| Leptin | | | | | 20 nM | 2,5 ± 0,2* | 37 |

TABLE 7

Anxiolytic activity of 1-methoxy-carbonylmethyl-3-arylamino-1,3-dihydro-2H-benzo[e][1,4]diazepin-2-ones (Ib)

| No | $R^1$ | $R^2$ | $R^4$ | $R^5$ | Anxiolytic activity assessed using conflict situation method (5 mg/kg) | General movement activity (5 mg/kg) |
|----|-------|-------|-------|-------|------------------------------------------------------------------------|-------------------------------------|
| 89 | Br | $CH_2COOCH_3$ | F | 2-$COCH_3$ | 3.4 ± 1.2 | 40.0 ± 2.7 |
| 90 | Br | $CH_2COOCH_3$ | F | 3-$COCH_3$ | 8.2 ± 3.4 | 24.5 ± 2.3 |
| 91 | Br | $CH_2COOCH_3$ | F | 4-$COCH_3$ | 4.9 ± 2.2 | 25.2 ± 2.1 |
| 173 | Cl | $CH_2COOCH_3$ | H | 2-$NO_2$ | 120.5 ± 10.3 | 15.0 ± 1.3 |
| 174 | Cl | $CH_2COOCH_3$ | H | 3-$NO_2$ | 60.6 ± 7.0 | 18.0 ± 2.4 |
| 175 | Cl | $CH_2COOCH_3$ | H | 4-$NO_2$ | 48.7 ± 3.6 | 20.0 ± 1.0 |
| 227 | $OCF_3$ | $CH_2COOCH_3$ | H | 2-$NO_2$ | 109.5 ± 8.3 | 13.0 ± 1.3 |
| 228 | $OCF_3$ | $CH_2COOCH_3$ | H | 3-$NO_2$ | 40.6 ± 3.9 | 17.0 ± 2.4 |
| 229 | $OCF_3$ | $CH_2COOCH_3$ | H | 4-$NO_2$ | 38.7 ± 2.6 | 19.0 ± 1.0 |
| 281 | $NO_2$ | $CH_2COOCH_3$ | H | 2-$NO_2$ | 115.6 ± 9.3 | 14.0 ± 1.4 |
| 282 | $NO_2$ | $CH_2COOCH_3$ | H | 3-$NO_2$ | 44.7 ± 3.9 | 19.0 ± 2.4 |
| 283 | $NO_2$ | $CH_2COOCH_3$ | H | 4-$NO_2$ | 45.1 ± 2.6 | 22.0 ± 2.0 |
| 317 | $NO_2$ | $CH_2COOCH_3$ | Cl | 2-F | 33.4 ± 3.2 | 47.0 ± 3.7 |
| 318 | $NO_2$ | $CH_2COOCH_3$ | Cl | 3-F | 19.2 ± 3.4 | 28.5 ± 2.3 |
| 319 | $NO_2$ | $CH_2COOCH_3$ | Cl | 4-F | 18.1 ± 2.2 | 27.2 ± 2.1 |
| 326 | $NO_2$ | $CH_2COOCH_3$ | Cl | 2-Br | 45.1 ± 2.6 | 22.0 ± 2.0 |
| 327 | $NO_2$ | $CH_2COOCH_3$ | Cl | 3-Br | 43.4 ± 3.2 | 45.0 ± 3.7 |
| 328 | $NO_2$ | $CH_2COOCH_3$ | Cl | 4-Br | 23.2 ± 3.4 | 24.5 ± 2.3 |
| 362 | $NO_2$ | $CH_2COOCH_3$ | F | 2-Cl | 35.1 ± 3.5 | 29.2 ± 2.3 |
| 363 | $NO_2$ | $CH_2COOCH_3$ | F | 3-Cl | 46.4 ± 4.2 | 41.0 ± 3.9 |
| 364 | $NO_2$ | $CH_2COOCH_3$ | F | 4-Cl | 26.2 ± 3.4 | 34.5 ± 3.3 |
| 398 | $NO_2$ | $CH_2COOCH_3$ | F | 2-$CF_3$ | 33.1 ± 3.2 | 28.2 ± 3.3 |
| 399 | $NO_2$ | $CH_2COOCH_3$ | F | 3-$CF_3$ | 44.4 ± 4.3 | 41.8 ± 4.3 |
| 400 | $NO_2$ | $CH_2COOCH_3$ | F | 4-$CF_3$ | 32.2 ± 3.3 | 36.5 ± 3.3 |
| Diazepam | | | | | 120.0 ± 4.9 | 32.5 ± 2.8 |
| Control | | | | | 9.0 ± 1.1 | 35.0 ± 1.5 |

The invention claimed is:

1. Compounds having a formula I

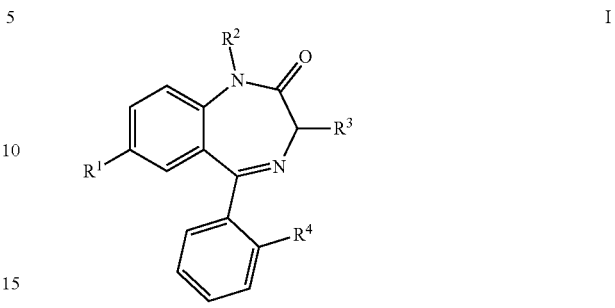

wherein:
when $R^1$ is Br, then $R^4$ is F;
when $R^1$ is $OCF_3$, then $R^4$ is H;
when $R^1$ is $NO_2$, then $R^4$ is Cl;
when $R^1$ is $NO_2$, then $R^4$ is F;
when $R^2$ is selected from the group consisting of H, $CH_2COCH_3$, $CH_2COOCH_3$, and $CH_2CONHNH_2$;
then $R^3$ is selected from the group consisting of OAlk and NHAr, wherein
Alk selected from the group consisting of $C_2H_5$, $C_3H_7$, $C_4H_9$, $(CH_2)_2OH$, $(CH_2)_2OCH_3$, and

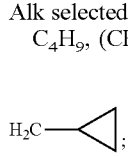

and

Ar is

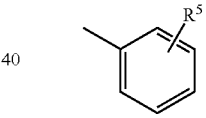

wherein $R^5$ is selected from the group consisting of o-$COCH_3$, m-$COCH_3$, p-$COCH_3$, Cl, F, Br, $NO_2$, and $CF_3$.

2. Compounds having a formula I

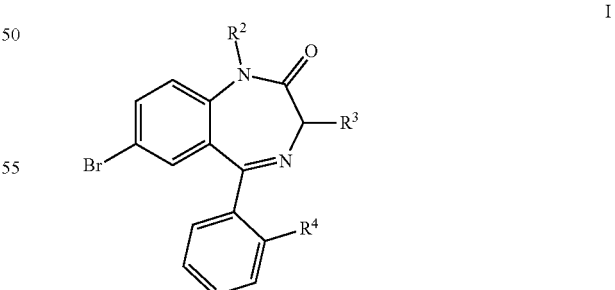

wherein:
$R^1$ is Cl;
$R^2$ is selected from the group consisting of H, $CH_2COCH_3$, $CH_2COOCH_3$, and $CH_2CONHNH_2$;
wherein when $R^2$ is H, then $R^3$ is selected from the group consisting of OAlk and NHAr, wherein Alk is selected from the group consisting of (CH$_2$)$_2$OCH$_3$ and

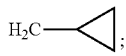

and
Ar is

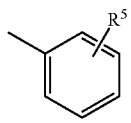

wherein R$^5$ is selected from the group consisting of m-COCH$_3$, p-COCH$_3$, o-F, m-F, p-F, Br and CF$_3$;
wherein when R$^2$ is selected from the group consisting of CH$_2$COCH$_3$, CH$_2$COOCH$_3$, and CH$_2$CONHNH$_2$, then R$^3$ is selected from the group consisting of OAlk and NHAr, wherein
Alk is selected from the group consisting of C$_2$H$_5$, C$_3$H$_7$, C$_4$H$_9$, (CH$_2$)$_2$OH, (CH$_2$)$_2$OCH$_3$ and

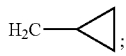

and
Ar is

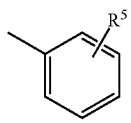

wherein R$^5$ is selected from the group consisting of o-COCH$_3$, m-COCH$_3$, p-COCH$_3$, Cl, F, Br, NO$_2$, and CF$_3$; and
R$^4$ is H.

3. Compounds having a formula I

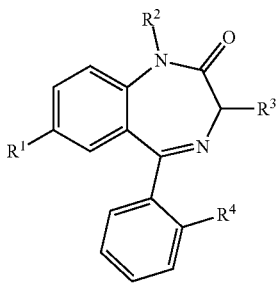

I wherein
R$^1$ is NO$_2$,
R$^2$ is selected from the group consisting of H, CH$_2$COCH$_3$, CH$_2$COOCH$_3$, and CH$_2$CONHNH$_2$;
wherein when R$^2$ is H, then R$^3$ is selected from the group consisting of OAlk and NHAr, wherein
Alk is selected from the group consisting of (CH$_2$)$_2$OCH$_3$ and

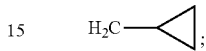

and
Ar is

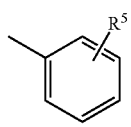

wherein R$^5$ is selected from the group consisting of o-COCH$_3$, m-COCH$_3$, p-COCH$_3$, Cl, F, Br, NO$_2$ and CF$_3$;
wherein when R$^2$ is selected from the group consisting of CH$_2$COCH$_3$, CH$_2$COOCH$_3$, and CH$_2$CONHNH$_2$; then R$^3$ is selected from the group consisting of OAlk and NHAr, wherein
Alk is selected from the group consisting of C$_2$H$_5$, C$_3$H$_7$, C$_4$H$_9$, (CH$_2$)$_2$OH, (CH$_2$)$_2$OCH$_3$ and

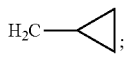

and
Ar is

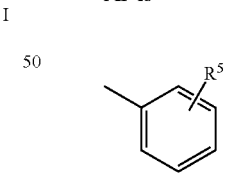

wherein R$^5$ is selected from the group consisting of o-COCH$_3$, m-COCH$_3$, p-COCH$_3$, Cl, F, Br, NO$_2$, CF$_3$; and
R$^4$=H.

* * * * *